US009688724B2

(12) United States Patent
Rodgers et al.

(10) Patent No.: US 9,688,724 B2
(45) Date of Patent: Jun. 27, 2017

(54) METHODS FOR LIMITING DEVELOPMENT OF A SKIN WOUND

(71) Applicant: University of Southern California, Los Angeles, CA (US)

(72) Inventors: Kathleen E. Rodgers, Long Beach, CA (US); Gere S. diZerega, San Luis Obispo, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/401,013

(22) PCT Filed: Mar. 14, 2013

(86) PCT No.: PCT/US2013/031375
§ 371 (c)(1),
(2) Date: Nov. 13, 2014

(87) PCT Pub. No.: WO2013/172956
PCT Pub. Date: Nov. 21, 2013

(65) Prior Publication Data
US 2015/0147283 A1 May 28, 2015

Related U.S. Application Data

(60) Provisional application No. 61/646,493, filed on May 14, 2012, provisional application No. 61/726,828, filed on Nov. 15, 2012.

(51) Int. Cl.
| | |
|---|---|
| *A61K 38/00* | (2006.01) |
| *C07K 9/00* | (2006.01) |
| *C07K 7/14* | (2006.01) |
| *A61K 38/08* | (2006.01) |
| *A61K 9/00* | (2006.01) |
| *A61K 47/14* | (2017.01) |
| *A61K 9/06* | (2006.01) |
| *A61K 47/38* | (2006.01) |
| *A61F 13/00* | (2006.01) |

(52) U.S. Cl.
CPC .............. *C07K 7/14* (2013.01); *A61K 9/0014* (2013.01); *A61K 9/06* (2013.01); *A61K 38/085* (2013.01); *A61K 47/14* (2013.01); *A61K 47/38* (2013.01); *A61F 2013/0051* (2013.01); *A61F 2013/00365* (2013.01); *A61F 2013/00404* (2013.01); *A61F 2013/00519* (2013.01); *A61F 2013/00902* (2013.01); *A61F 2013/00927* (2013.01); *A61F 2013/00982* (2013.01)

(58) Field of Classification Search
None
See application file for complete search history.

(56) References Cited

U.S. PATENT DOCUMENTS

| | | | |
|---|---|---|---|
| 5,585,398 A * | 12/1996 | Ernst | A61K 31/245 514/535 |
| 5,834,432 A | 11/1998 | diZerega | |
| 5,955,430 A | 9/1999 | diZerega | |
| 6,096,709 A | 8/2000 | diZerega | |
| 6,110,895 A * | 8/2000 | Rodgers | A61K 38/085 514/9.7 |
| 6,165,978 A | 12/2000 | diZerega | |
| 6,177,407 B1 | 1/2001 | diZerega et al. | |
| 6,239,109 B1 | 5/2001 | diZerega et al. | |
| 6,248,587 B1 | 6/2001 | Rodgers et al. | |
| 6,258,778 B1 | 7/2001 | diZerega et al. | |
| 6,335,195 B1 | 1/2002 | Rodgers et al. | |
| 6,444,646 B1 | 9/2002 | Rodgers et al. | |
| 6,455,500 B1 | 9/2002 | diZerega et al. | |
| 6,455,501 B1 | 9/2002 | Rodgers et al. | |
| 6,475,988 B1 | 11/2002 | Rodgers et al. | |
| 6,482,800 B1 | 11/2002 | Rodgers et al. | |
| 6,498,138 B1 | 12/2002 | Rodgers et al. | |
| 6,730,775 B1 | 5/2004 | diZerega et al. | |
| 6,747,008 B1 | 6/2004 | diZerega et al. | |
| 6,762,167 B1 | 7/2004 | Rodgers et al. | |
| 6,821,953 B1 | 11/2004 | diZerega et al. | |
| 6,916,783 B2 | 7/2005 | Rodgers et al. | |
| 7,022,675 B2 | 4/2006 | DiZerega | |
| 7,118,748 B1 | 10/2006 | Rodgers et al. | |
| 7,122,523 B2 | 10/2006 | Rodgers et al. | |
| 7,173,011 B2 | 2/2007 | Rodgers et al. | |
| 7,176,183 B2 | 2/2007 | diZerega et al. | |
| 7,288,522 B1 | 10/2007 | diZerega et al. | |
| 7,338,938 B2 | 3/2008 | Rodgers et al. | |
| 7,744,927 B2 | 6/2010 | Rodgers et al. | |
| 7,745,411 B2 | 6/2010 | diZerega et al. | |
| 7,776,828 B2 | 8/2010 | diZerega et al. | |
| 7,786,085 B2 | 8/2010 | diZerega et al. | |
| 8,207,233 B1 | 6/2012 | Rodgers et al. | |
| 8,207,234 B1 | 6/2012 | Rodgers et al. | |
| 8,536,231 B2 | 9/2013 | Rodgers et al. | |
| 2003/0130196 A1 | 7/2003 | Rodgers | |

FOREIGN PATENT DOCUMENTS

| | | |
|---|---|---|
| WO | 2008/018792 | 2/2008 |
| WO | 2009/124266 A2 | 10/2009 |
| WO | 2011/120032 A1 | 9/2011 |

OTHER PUBLICATIONS

Rodgers, et al. "Accelerated healing of diabetic wounds by NorLeu(3)-angiotensin (1-7)," Expert Opinion on Investigational Drugs, 20(11): 1575-1584, 2011.
Rodgers, et al., "Effect of NorLeu3-A(1-7) on scar formation over time after full-thickness incision injury in the rat," Wound Repair and Regeneration, Mosby-Year Book, St. Louis, vol. 13, No. 3:309-317, 2005.

(Continued)

*Primary Examiner* — Jeanette Lieb
(74) *Attorney, Agent, or Firm* — McDonnell Boehnen Hulbert & Berghoff LLP

(57) ABSTRACT

The present invention provides methods for limiting development of skin wounds, and also for treatment of one or more of erythemas, blisters, rashes, pruritis, contact dermatitis, psoriasis, eczema, acne, and athlete's foot.

22 Claims, 7 Drawing Sheets

(56) References Cited

OTHER PUBLICATIONS

Rodgers, et al., "Histological evaluation of the effects of angiotensin peptides on wound repair in diabetic mice," Experimental Dermatology, 12(6): 784-790, 2003.

Fried, et al., "Application of angiogenesis to clinical dermatology," Advances in Dermatology, 24: 89-103, 2008.

International Search Report for PCT/US2013/031375, mailed Jun. 27, 2013.

Regoli, et al., Pharmacological Reviews 26:69 (1974).

Pinheiro et al., Hypertension. Oct. 2004;44(4):490-6. Epub Aug. 23, 2004.

Kumar, et al. (2008). Radiation-induced skin injury in the animal model of scleroderma: implications for post-radiotherapy fibrosis. Radiation Oncology, 3:40-47.

Ouhtit, et al. (2000). Temporal events in skin injury and the early adaptive responses in ultraviolet-irradiated mouse skin. Am J Pathol, 156(1):201-207.

Withers, et al. (1977). Effect of dose fractionation on early and late skin responses to $\gamma$-rays and neutrons. Intl. Journal. Radiation Oncology Biol. Phys. 3:227-233.

\* cited by examiner

SEQUENCE LISTING

```
<160> NUMBER OF SEQ ID NOS: 51

<210> SEQ ID NO 1
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H, Asp, Glu, Asn, Acpc
      (1-aminocyclopentane carboxylic acid), Ala, Me2Gly, Pro, Bet,
      Glu(NH2), Gly, Asp(NH2), Suc, or is absent,
<220> FEATURE:
```

```
<221> NAME/KEY: MISC_FEATURE
<222> LOCATION: (2)..(2)
<223> OTHER INFORMATION: Xaa is Arg, Lys, Ala, Cit, Orn, Ser(Ac), Sar,
      D-Arg or D-Lys
<220> FEATURE:
<221> NAME/KEY: MISC_FEATURE
<222> LOCATION: (3)..(3)
<223> OTHER INFORMATION: Xaa is Val, Ala, Leu, norLeu, Ile, Gly, Lys,
      Pro, Aib, Acpc or Tyr
<220> FEATURE:
<221> NAME/KEY: MISC_FEATURE
<222> LOCATION: (4)..(4)
<223> OTHER INFORMATION: Xaa is Tyr, Tyr(PO3)2, Thr, Ser, homoSer,
      azaTyr, or Ala
<220> FEATURE:
<221> NAME/KEY: MISC_FEATURE
<222> LOCATION: (5)..(5)
<223> OTHER INFORMATION: Xaa is Ile, Ala, Leu, norLeu, Val or Gly
<220> FEATURE:
<221> NAME/KEY: MISC_FEATURE
<222> LOCATION: (6)..(6)
<223> OTHER INFORMATION: Xaa is His, Arg or 6-NH2-Phe
<220> FEATURE:
<221> NAME/KEY: MISC_FEATURE
<222> LOCATION: (7)..(7)
<223> OTHER INFORMATION: Xaa is Pro or Ala
<220> FEATURE:
<221> NAME/KEY: MISC_FEATURE
<222> LOCATION: (8)..(8)
<223> OTHER INFORMATION: Xaa is Phe, Phe(Br), Ile and Tyr, excluding
      sequences including R4 as a terminal Tyr group

<400> SEQUENCE: 1

Xaa Xaa Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Arg Val Tyr Ile His Pro Phe
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Val Tyr Ile His Pro Phe
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Asp Arg Val Tyr Ile His Pro
1               5

<210> SEQ ID NO 5
<211> LENGTH: 6
```

```
<212> TYPE: PRT
<213> ORGANISM: Artificial Sequence
<220> FEATURE:
<223> OTHER INFORMATION: Synthetic

<400> SEQUENCE: 5

Arg Val Tyr Ile His Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Val Tyr Ile His Pro
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Ile His Pro Phe
1

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Asp Arg Val Tyr Ile His
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Asp Arg Val Tyr Ile
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Asp Arg Val Tyr
1

<210> SEQ ID NO 11
<211> LENGTH: 7
<212> TYPE: PRT
```

```
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Nle

<400> SEQUENCE: 11

Arg Leu Tyr Ile His Pro Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Nle

<400> SEQUENCE: 12

Arg Val Tyr Leu His Pro Phe
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Asp Arg Pro Tyr Ile His Pro Phe
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 14

Asp Arg Leu Tyr Ile His Pro
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Asp, Glu or absent
<220> FEATURE:
<221> NAME/KEY: MISC_FEATURE
<222> LOCATION: (2)..(2)
<223> OTHER INFORMATION: Xaa is Arg, Lys, or Ala
<220> FEATURE:
<221> NAME/KEY: MISC_FEATURE
<222> LOCATION: (3)..(3)
<223> OTHER INFORMATION: Xaa is Val, Ala, Leu, norLeu, Ile, Gly, Lys, or
```

```
        Pro
<220> FEATURE:
<221> NAME/KEY: MISC_FEATURE
<222> LOCATION: (4)..(4)
<223> OTHER INFORMATION: Xaa is Tyr or homoSer
<220> FEATURE:
<221> NAME/KEY: MISC_FEATURE
<222> LOCATION: (5)..(5)
<223> OTHER INFORMATION: Xaa is Ile, Ala, Leu, norLeu, Val or Gly
<220> FEATURE:
<221> NAME/KEY: MISC_FEATURE
<222> LOCATION: (6)..(6)
<223> OTHER INFORMATION: Xaa is His or Arg
<220> FEATURE:
<221> NAME/KEY: MISC_FEATURE
<222> LOCATION: (7)..(7)
<223> OTHER INFORMATION: Xaa is Pro or Ala
<220> FEATURE:
<221> NAME/KEY: MISC_FEATURE
<222> LOCATION: (8)..(8)
<223> OTHER INFORMATION: Xaa is Phe, Ile or is absent

<400> SEQUENCE: 15

Xaa Xaa Xaa Xaa Xaa Xaa Xaa Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 16

Asp Arg Leu Tyr Ile
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 17

Asp Arg Leu Tyr Ile His
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Asp Arg Val Tyr Val His Pro Phe
1               5

<210> SEQ ID NO 19
<211> LENGTH: 8
<212> TYPE: PRT
<213> ORGANISM: Artificial Sequence
```

```
<220> FEATURE:
<223> OTHER INFORMATION: Synthetic

<400> SEQUENCE: 19

Asn Arg Val Tyr Val His Pro Phe
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Ala Pro Gly Asp Arg Ile Tyr Val His Pro Phe
1               5                   10

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Glu Arg Val Tyr Ile His Pro Phe
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Asp Lys Val Tyr Ile His Pro Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Asp Arg Ala Tyr Ile His Pro Phe
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Asp Arg Val Thr Ile His Pro Phe
1               5

<210> SEQ ID NO 25
<211> LENGTH: 8
<212> TYPE: PRT
<213> ORGANISM: Artificial Sequence
<220> FEATURE:
```

<223> OTHER INFORMATION: Synthetic

<400> SEQUENCE: 25

Asp Arg Val Tyr Leu His Pro Phe
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Asp Arg Val Tyr Ile Arg Pro Phe
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Asp Arg Val Tyr Ile His Ala Phe
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Asp Arg Val Tyr Ile His Pro Tyr
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Pro Arg Val Tyr Ile His Pro Phe
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Tyr is Try(PO3)2

<400> SEQUENCE: 30

Asp Arg Val Tyr Ile His Pro Phe
1               5

<210> SEQ ID NO 31
<211> LENGTH: 8

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 31

Asp Arg Leu Tyr Ile His Pro Phe
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: Nle

<400> SEQUENCE: 32

Asp Arg Val Tyr Leu His Pro Phe
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: homoSer

<400> SEQUENCE: 33

Asp Arg Val Ser Tyr Ile His Pro Phe
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H, Arg, Lys, Ala, Orn, Citron, Ser(Ac),
     Sar, D-Arg or D-Lys
<220> FEATURE:
<221> NAME/KEY: MISC_FEATURE
<222> LOCATION: (2)..(2)
<223> OTHER INFORMATION: Xaa is Val, Ala, Leu, norLeu, Ile, Gly, Lys,
     Pro, Aib, Acpc or Tyr
<220> FEATURE:
<221> NAME/KEY: MISC_FEATURE
<222> LOCATION: (3)..(3)
<223> OTHER INFORMATION: Xaa is Tyr, Tyr(PO3)2, Thr, Ser, homoSer,
     azaTyr, or Ala
<220> FEATURE:
<221> NAME/KEY: MISC_FEATURE
<222> LOCATION: (4)..(4)
<223> OTHER INFORMATION: Xaa is Ile, Ala, Leu, norLeu, Val or Gly
<220> FEATURE:
<221> NAME/KEY: MISC_FEATURE
<222> LOCATION: (5)..(5)
<223> OTHER INFORMATION: Xaa is His, Arg or 6-NH2-Phe
<220> FEATURE:
```

```
<221> NAME/KEY: MISC_FEATURE
<222> LOCATION: (6)..(6)
<223> OTHER INFORMATION: Xaa is Pro or Ala
<220> FEATURE:
<221> NAME/KEY: MISC_FEATURE
<222> LOCATION: (7)..(7)
<223> OTHER INFORMATION: Xaa is Phe, Phe(Br), Ile or Tyr, excluding
      sequences including R4 as a terminal Tyr group

<400> SEQUENCE: 34

Xaa Xaa Xaa Xaa Xaa Xaa Xaa
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, Ala, Cit, Orn, Ser(Ac), Sar,
      D-Arg or D-Lys
<220> FEATURE:
<221> NAME/KEY: MISC_FEATURE
<222> LOCATION: (2)..(2)
<223> OTHER INFORMATION: Xaa is Val, Ala, Leu, norLeu, Ile, Gly, Lys,
      Pro, Aib, Acpc or Tyr
<220> FEATURE:
<221> NAME/KEY: MISC_FEATURE
<222> LOCATION: (4)..(4)
<223> OTHER INFORMATION: Xaa is Ile, Ala, Leu, norLeu, Val or Gly

<400> SEQUENCE: 35

Xaa Xaa Tyr Xaa His Pro Phe
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Arg Val Tyr Gly His Pro Phe
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Arg Val Tyr Ala His Pro Phe
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Asp Arg Val Ala Ile His Pro
1               5
```

<210> SEQ ID NO 39
<211> LENGTH: 7
<212> TYPE: PRT
<213> ORGANISM: Artificial Sequence
<220> FEATURE:
<223> OTHER INFORMATION: Synthetic

<400> SEQUENCE: 39

Asp Arg Pro Tyr Ile His Pro
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Asp Arg Lys Tyr Ile His Pro
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 41

Asp Arg Leu Tyr Ile His Pro
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Asp Arg Val Tyr Ile His Pro Ile
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Arg Val Ala Ile His Pro Phe
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

```
Arg Val Ala Ile His Pro Phe
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic

<400> SEQUENCE: 45

Gly Arg Val Tyr Ile His Pro Phe
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Nle

<400> SEQUENCE: 46

Arg Val Tyr Leu His Pro Phe
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: C-terminal 1-aminocyclopentane carboxylic acid

<400> SEQUENCE: 47

Asp Arg Tyr Ile His Pro Phe
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Orn

<400> SEQUENCE: 48

Asp Xaa Val Tyr Ile His Pro Phe
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: C-terminal Citron
```

```
<400> SEQUENCE: 49

Asp Val Tyr Ile His Pro Phe
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic

<400> SEQUENCE: 50

Asp Arg Pro Ala Ile His Pro
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: 3Hyp

<400> SEQUENCE: 51

Asp Arg Pro Ala Ile His Pro
1               5
```

METHODS FOR LIMITING DEVELOPMENT OF A SKIN WOUND

CROSS REFERENCE

This application is a U.S. National Phase of International Application No. PCT/US2013/031375, filed Mar. 14, 2013, which claims priority to U.S. Provisional Application No. 61/646,493, filed May 14, 2012 and U.S. Provisional Application No. 61/726,828, filed Nov. 15, 2012, the disclosures of which are hereby incorporated by reference in their entireties.

STATEMENT OF GOVERNMENT RIGHTS

This invention was made with government support under Biomedical Advanced Research and Development Authority (BARDA) grant number 09-34. The government has certain rights in the invention.

BACKGROUND OF THE INVENTION

Epithelial injury following low-penetrating radiation can result in lesions from direct exposure or indirectly by damage to epithelial progenitor cells that would otherwise contribute to healing and inflammation. Methods for limiting development of skin wounds in the radiation exposure context and in other contexts are needed in the art.

SUMMARY OF THE INVENTION

In one aspect, the present invention provides methods for limiting development of a skin wound, comprising administering to a subject at risk of developing a wound an amount effective of a polypeptide comprising or consisting of angiotensinogen, angiotensin I (AI), AI analogues, AI fragments and analogues thereof, angiotensin II (AII), AII analogues, AII fragments or analogues thereof, AII $AT_2$ type 2 receptor agonists, or an agonist (polypeptide or otherwise) of the MAS receptor. In one embodiment, the subject is at risk for developing a wound due to exposure to an injurious agent selected from the group consisting of allergens (food, dyes, medicine, insect bites or stings, metals, etc.), skin contact with an irritant (chemical agent, mechanical (clothing, etc.), thermal, radiative etc.), psoriasis, eczema, acne, excessive sun exposure, friction due to chafing of skin, exposure to ionizing radiation, friction on the skin (including but not limited to poor-fitting shoes and other clothing heat exposure, cold exposure (including but not limited to frostbite), chemical exposure (including but not limited to cosmetic, detergent, solvent, etc.), contact dermatitis, vesicants (including but not limited to mustard gas and Lewisite); crunching, pinching, or squeezing of the skin; scabies, swimmers' itch, athlete's foot, exposure to poison ivy, exposure to poison oak; body, pubic, or head lice; insect hives, abrasion, contusion, dehydration, excoriation, sound including but not limited to ultrasound, viruses (such as Herpes Simplex), autoimmune disease (such as systemic lupus erythematosus), and xerosis. In another embodiment, the subject has developed a "pre-wound" indication prior to treatment as a result of exposure to the injurious agent, wherein the pre-wound indication includes but is not limited to erythemas, blisters, rashes, and pruritis.

In another aspect, the present invention provides methods for treating erythemas, blisters, rashes, and/or pruritis, comprising administering to a subject in need thereof an amount effective of a polypeptide comprising or consisting of angiotensinogen, angiotensin I (AI), AI analogues, AI fragments and analogues thereof, angiotensin II (AII), AII analogues, AII fragments or analogues thereof, AII $AT_2$ type 2 receptor agonists, or an agonist (polypeptide or otherwise) of the MAS receptor, to treat the erythema, blister, rash, and/or pruritis.

In a further aspect, the present invention provides methods for treating a disorder selected from the group consisting of contact dermatitis, psoriasis, eczema, acne, and athlete's foot, comprising administering to a subject in need thereof an amount effective of a polypeptide comprising or consisting of angiotensinogen, angiotensin I (AI), AI analogues, AI fragments and analogues thereof, angiotensin II (AII), AII analogues, AII fragments or analogues thereof, AII $AT_2$ type 2 receptor agonists, or an agonist (polypeptide or otherwise) of the MAS receptor, to treat the disorder.

In one preferred embodiment of any of the above aspects, embodiments, and combinations thereof, the subject is administered a polypeptide comprising or consisting of at least 5 contiguous amino acids of the peptide Asp-Arg-Nle-Tyr-Ile-His-Pro (SEQ ID NO: 14).

DETAILED DESCRIPTION OF THE INVENTION

Figure 1:
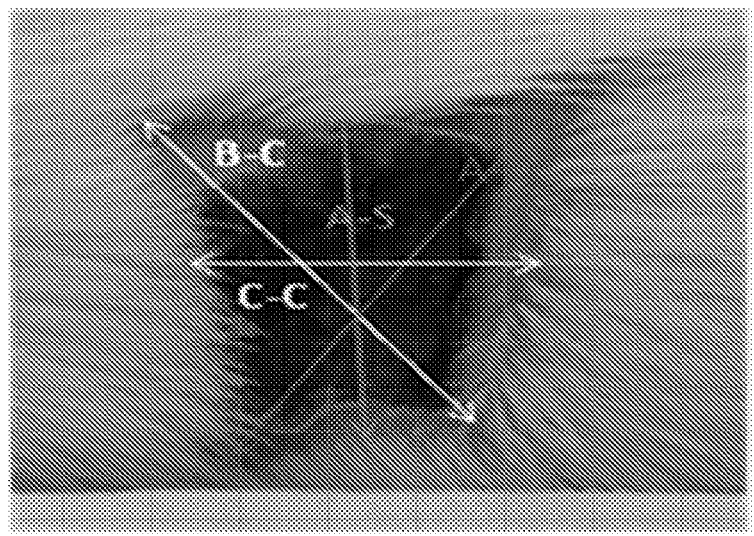
FIG. 1 shows an example of measurements of exposed skin as detailed in the Example 1.
Figure 2A:
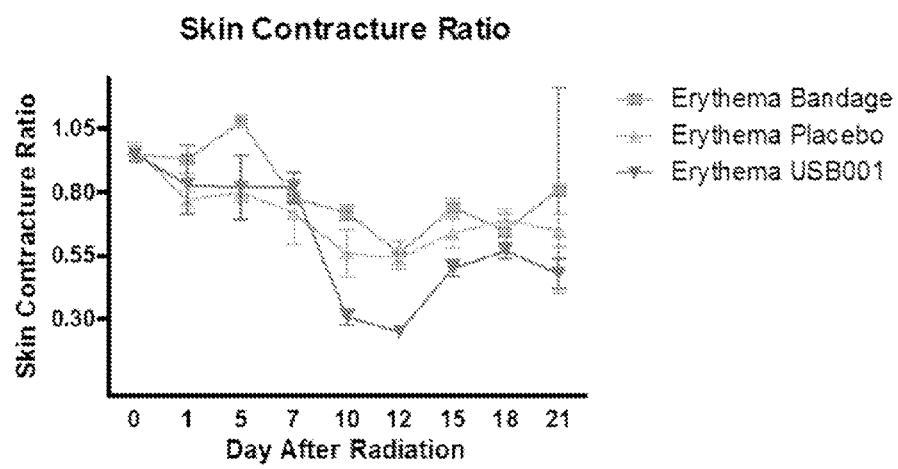
FIGS. 2A-D show a summary of results from gross evaluation level of the skin after exposure to 32 Gy low penetrating radiation. Histological sections were prepared at day 30 and evaluated for skin contracture ratio (2A), Kumar mean score (2B), inflammation in the upper dermis (2C) and inflammation above the adipose (2D). The control group consists of non-irradiated, non-treated animals necropsied on day 30.
Figure 2B:
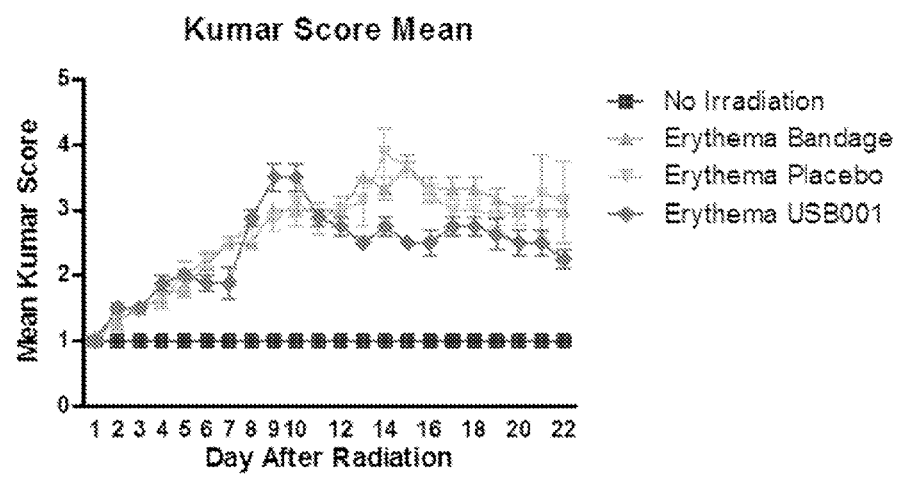
Figure 2C:
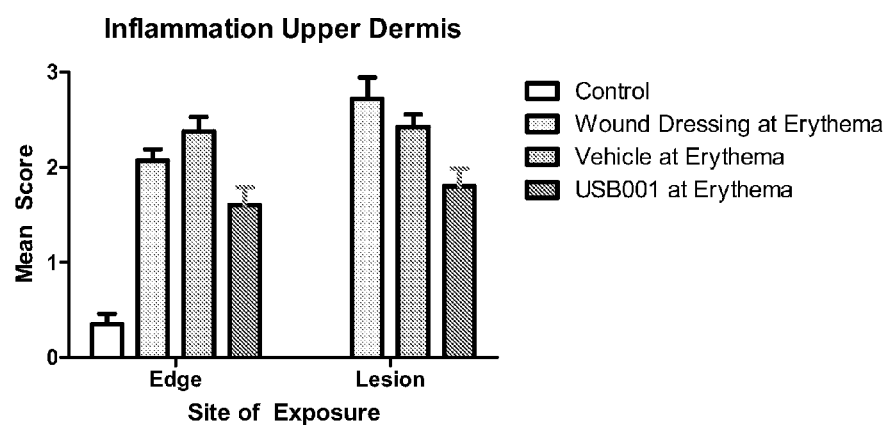
Figure 2D:
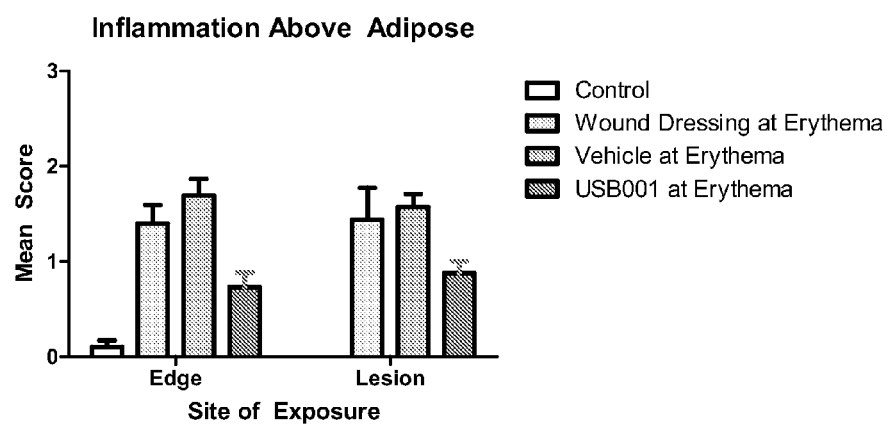

As used herein, the singular forms "a," "an" and "the" include plural referents unless the context clearly dictates otherwise. "And" as used herein is interchangeably used with "or" unless expressly stated otherwise.

All embodiments within and between different aspects of the invention can be combined unless the context clearly dictates otherwise.

As used herein, the term "about" means +/−5% of the relevant measurement or unit.

In a first aspect, the present invention provides methods for limiting development of a skin wound, comprising administering to a subject at risk of developing a wound an amount effective of a polypeptide comprising or consisting of angiotensinogen, angiotensin I (AI), AI analogues, AI fragments and analogues thereof, angiotensin II (AII), AII analogues, AII fragments or analogues thereof, AII $AT_2$ type 2 receptor agonists, or an agonist (polypeptide or otherwise) of the MAS receptor.

The inventors have surprisingly discovered that the methods of the invention can be used to limit development of skin wounds in subjects that have been exposed to an injurious agent and have not yet developed a wound.

The subject may be any suitable mammalian subject, such as a human subject, that has been exposed to an injurious agent but has not yet developed a wound. As used herein a "wound" is a laceration (i.e.: cut) or opening in the skin, such as an ulcer.

Thus, the subjects of the invention have not yet developed a wound as a result of exposure to the injurious agent, but may have developed a "pre-wound" indication, including but not limited to erythemas, blisters, rashes, and pruritis.

As used herein, "erythemas" are redness of the skin, generally caused by hyperemia of the capillaries in the lower layers of the skin.

As used herein, "blisters" are pockets of fluid within the upper layers of the skin, typically caused by friction, burning, freezing, chemical exposure or infection. Blisters can be filled with plasma, blood, or pus.

As used herein, "rashes" are changes in color, appearance or texture of the skin. A rash may be localized in one part of the body, or affect all the skin. Rashes may cause the skin to change color, itch, become warm, bumpy, chapped, dry, cracked or blistered, swell and may be painful.

As used herein, "pruritis" is a sensation that causes the desire or reflex to scratch.

As used herein, an "injurious agent" is one that may ultimately result in development of a wound, and may cause a "pre-wound" indication, including but not limited to erythemas, blisters, rashes, and pruritis. Examples of such injurious agents include, but are not limited to allergens (food, dyes, medicine, insect bites or stings, metals, etc.), skin contact with an irritant (chemical agent, mechanical (clothing, etc.), thermal, radiative etc.), psoriasis, eczema, acne, excessive sun exposure, friction due to chafing of skin, exposure to ionizing radiation, friction on the skin (including but not limited to poor-fitting shoes and other clothing heat exposure, cold exposure (including but not limited to frostbite), chemical exposure (including but not limited to cosmetic, detergent, solvent, etc.), contact dermatitis, vesicants (including but not limited to mustard gas and Lewisite); crunching, pinching, or squeezing of the skin; scabies, swimmers' itch, athlete's foot, exposure to poison ivy, exposure to poison oak; body, pubic, or head lice; insect hives, abrasion, contusion, dehydration, excoriation, sound including but not limited to ultrasound, viruses (such as Herpes Simplex), autoimmune disease (such as systemic lupus erythematosus), and xerosis.

As used herein, "limiting development of a wound" means accomplishing one or more of the following: (a) slowing the time to wound development resulting from exposure to an injurious agent; (b) decreasing or slowing rate of progression of the severity (including but not limited to size, depth, duration, and/or associated pain) of a subsequently developed wound resulting from exposure to an injurious agent; and (c) preventing wound development resulting from exposure to an injurious agent.

In one non-limiting example, the injurious agent is a burn source, such as the sun, a source of thermal heat, or a radiation source. In this embodiment, the method may comprise administering to the subject at risk of developing a wound an amount effective of a polypeptide to reduce the subsequent (i.e.: post-treatment) extent and/or severity of sunburn, thermal burn, or radiation burn, such as by reducing the extent and/or severity of subsequent loss of dermal integrity loss, including ulceration.

In one embodiment, the polypeptides for use in the invention comprise or consist of a sequence of at least four contiguous amino acids of groups $R^1$-$R^8$ in the sequence of general formula I $$R^1-R^2-R^3-R^4-R^5-R^6-R^7-R^8 \quad \text{(SEQ ID NO: 1)}$$

wherein $R^1$ is selected from the group consisting of H, Asp, Glu, Asn, Acpc (1-aminocyclopentane carboxylic acid), Ala, $Me^2$Gly, Pro, Bet, Glu($NH_2$), Gly, Asp($NH_2$) and Suc, or is absent, $R^2$ is selected from the group consisting of Arg, Lys, Ala, Cit, Orn, Ser(Ac), Sar, D-Arg and D-Lys, $R^3$ is selected from the group consisting of Val, Ala, Leu, norLeu, Ile, Gly, Lys, Pro, Aib, Acpc and Tyr;

$R^4$ is selected from the group consisting of Tyr, Tyr($PO_3$)$_2$, Thr, Ser, homoSer, azaTyr, and Ala;

$R^5$ is selected from the group consisting of Ile, Ala, Leu, norLeu, Val and Gly;

$R^6$ is selected from the group consisting of His, Arg or 6-$NH_2$-Phe;

$R^7$ is selected from the group consisting of Pro or Ala; and $R^8$ is selected from the group consisting of Phe, Phe(Br), Ile and Tyr, excluding sequences including $R^4$ as a terminal Tyr group.

Exemplary AT2 agonists useful in the practice of the invention include the AII analogues set forth above subject to the restriction that $R^6$ is p-$NH_2$-Phe.

In a further preferred embodiment of each of the above embodiments (SEQ ID NO: 15), $R^1$ is selected from the group consisting of Asp and Glu, or is absent;

$R^2$ is selected from the group consisting of Arg, Lys, and Ala;

$R^3$ is selected from the group consisting of Val, Ala, Leu, norLeu, Ile, Gly, Lys, and Pro;

$R^4$ is selected from the group consisting of Tyr and homoSer;

$R^5$ is selected from the group consisting of Ile, Ala, Leu, norLeu, Val and Gly;

$R^6$ is selected from the group consisting of His and Arg;

$R^7$ is selected from the group consisting of Pro or Ala; and $R^8$ is selected from the group consisting of Phe, Ile, or is absent.

In alternate embodiments, the polypeptides comprise or consist of at least five, six, seven, or eight contiguous amino acids of groups $R^1$-$R^8$ in the sequence of general formula I. In a further alternative, the polypeptides consist essentially of a sequence of at least four, five, six, seven, or eight contiguous amino acids of groups $R^1$-$R^8$ in the sequence of general formula I.

Particularly preferred combinations for $R^1$ and $R^2$ are Asp-Arg, Asp-Lys, Glu-Arg and Glu-Lys. Particularly preferred embodiments of this class include the following: AIII or AII(2-8), Arg-Val-Tyr-Ile-His-Pro-Phe [SEQ ID NO:2]; AII(3-8), also known as des1-AIII or AIV, Val-Tyr-Ile-His-Pro-Phe [SEQ ID NO:3]; AII(1-7), Asp-Arg-Val-Tyr-Ile-His-Pro [SEQ ID NO:4]; AII(2-7). Arg-Val-Tyr-Ile-His-Pro [SEQ ID NO:5]; AII(3-7), Val-Tyr-Ile-His-Pro [SEQ ID NO:6]; AII(5-8), Ile-His-Pro-Phe [SEQ ID NO:7]; AII(1-6), Asp-Arg-Val-Tyr-Ile-His [SEQ ID NO:8]; AII(1-5), Asp-Arg-Val-Tyr-Ile [SEQ ID NO:9]; AII(1-4), Asp-Arg-Val-Tyr [SEQ ID NO:10]; and AII(1-3), Asp-Arg-Val. Other preferred embodiments include: Arg-norLeu-Tyr-Ile-His-Pro-Phe [SEQ ID NO:11] and Arg-Val-Tyr-norLeu-His-Pro-Phe [SEQ ID NO:12]. Still another preferred embodiment encompassed within the scope of the invention is a peptide having the sequence Asp-Arg-Pro-Tyr-Ile-His-Pro-Phe [SEQ ID NO:13].

In a most preferred embodiment, the polypeptides for use in the present invention comprise or consists of at least 5 contiguous amino acids of Nle3 A(1-7).

Nle3 A(1-7) is a peptide consisting of the amino acid sequence Asp-Arg-Nle-Tyr-Ile-His-Pro (SEQ ID NO: 14). In various further embodiments, the peptide administered to the subject may be Asp-Arg-Nle-Tyr-Ile (SEQ ID NO: 16), Asp-Arg-Nle-Tyr-Ile-His (SEQ ID NO: 17), or most preferably Asp-Arg-Nle-Tyr-Ile-His-Pro (SEQ ID NO: 14).

Other preferred embodiments comprise or consist of

```
                                          SEQ ID NO: 18
Asp-Arg-Val-Tyr-Val-His-Pro-Phe

SEQ ID NO: 19
Asn-Arg-Val-Tyr-Val-His-Pro-Phe

SEQ ID NO: 20
Ala-Pro-Gly-Asp-Arg-Ile-Tyr-Val-His-Pro-Phe

SEQ ID NO: 21
Glu-Arg-Val-Tyr-Ile-His-Pro-Phe

SEQ ID NO: 22
Asp-Lys-Val-Tyr-Ile-His-Pro-Phe

SEQ ID NO: 23
Asp-Arg-Ala-Tyr-Ile-His-Pro-Phe

SEQ ID NO: 24
Asp-Arg-Val-Thr-Ile-His-Pro-Phe

SEQ ID NO: 25
Asp-Arg-Val-Tyr-Leu-His-Pro-Phe

SEQ ID NO: 26
Asp-Arg-Val-Tyr-Ile-Arg-Pro-Phe

SEQ ID NO: 27
Asp-Arg-Val-Tyr-Ile-His-Ala-Phe

SEQ ID NO: 28
Asp-Arg-Val-Tyr-Ile-His-Pro-Tyr

SEQ ID NO: 29
Pro-Arg-Val-Tyr-Ile-His-Pro-Phe

SEQ ID NO: 13
Asp-Arg-Pro-Tyr-Ile-His-Pro-Phe

SEQ ID NO: 30
Asp-Arg-Val-Tyr(PO₃)₂-Ile-His-Pro-Phe

SEQ ID NO: 31
Asp-Arg-norLeu-Tyr-Ile-His-Pro-Phe

SEQ ID NO: 32
Asp-Arg-Val-Tyr-norLeu-His-Pro-Phe

SEQ ID NO: 33
Asp-Arg-Val-homoSer-Tyr-Ile-His-Pro-Phe
```

Another class of polypeptides of particular interest in accordance with the present invention are those of the general formula II:

$$R^2-R^3-R^4-R^5-R^6-R^7-R^8 \quad \text{(SEQ ID NO: 34)}$$

in which $R^2$ is selected from the group consisting of H, Arg, Lys, Ala, Orn, Citron, Ser(Ac), Sar, D-Arg and D-Lys; $R^3$-$R^8$ are as defined above, and excluding sequences including $R^4$ as a terminal Tyr group.

A particularly preferred subclass of the compounds of general formula II has the formula:

$$R^2-R^3-\text{Tyr}-R^5-\text{His-Pro-Phe} \quad \text{[SEQ ID NO: 35]}$$

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:36] and Arg-Val-Tyr-Ala-His-Pro-Phe [SEQ ID NO:37].

In the above formulas, the standard three-letter abbreviations for amino acid residues are employed. Other residues are abbreviated as follows:

TABLE 1

| Abbreviation for Amino Acids | |
| --- | --- |
| Me²Gly | N,N-dimethylglycyl |
| Bet | 1-carboxy-N,N,N-trimethylmethanaminium hydroxide inner salt (betaine) |
| Suc | Succinyl |
| Phe (Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |
| Cit | Citron |
| Orn | Ornithine |
| NorLeu (Nle) | NorLeucine |
| HomoSer | HomoSerine (isotheronine) |

It has been suggested that AII and its analogues adopt either a gamma or a beta turn (Regoli, et al., *Pharmacological Reviews* 26:69 (1974)). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$. Alternatively, $R_2$ may be H, Ala, Orn, Citron, Ser(Ac), Sar, D-Arg, or D-Lys.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Lys, Val, Ala, Leu, norLeu, Ile, Gly, Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr $(PO_3)_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). It has also been found that $R^4$ can be Ala, and that it can be used for cyclization of angiotensin peptides.

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, and Val.

In the angiotensinogen, AI, AI analogues, AI fragments and analogues thereof, AII analogues, fragments and analogues of fragments of particular interest in accordance with the present invention, $R^6$ is His, Arg or 6-$NH_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro or Ala in order to provide the most desirable orientation of $R^8$. In position $R^8$, both a hydrophobic ring and an anionic carboxyl terminal appear to be particularly useful in binding of the analogues of interest to receptors; therefore, Tyr, Ile, Phe(Br), and especially Phe are preferred for purposes of the present invention.

Analogues of particular interest include the following:

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 18 |
| Analogue 2 | Asn-Arg-Val-Tyr-Val-His-Pro-Phe | SEQ ID NO: 19 |
| Analogue 3 | Ala-Pro-Gly-Asp-Arg-Ile-Tyr-Val-His-Pro-Phe | SEQ ID NO: 20 |
| Analogue 4 | Glu-Arg-Val-Tyr-Ile-His-Pro-Phe | SEQ ID NO: 21 |
| Analogue 5 | Asp-Lys-Val-Tyr-Ile-His-Pro-Phe | SEQ ID NO: 22 |
| Analogue 6 | Asp-Arg-Ala-Tyr-Ile-His-Pro-Phe | SEQ ID NO: 23 |
| Analogue 7 | Asp-Arg-Val-Thr-Ile-His-Pro-Phe | SEQ ID NO: 24 |
| Analogue 8 | Asp-Arg-Val-Tyr-Leu-His-Pro-Phe | SEQ ID NO: 25 |
| Analogue 9 | Asp-Arg-Val-Tyr-Ile-Arg-Pro-Phe | SEQ ID NO: 26 |
| Analogue 10 | Asp-Arg-Val-Tyr-Ile-His-Ala-Phe | SEQ ID NO: 27 |
| Analogue 11 | Asp-Arg-Val-Tyr-Ile-His-Pro-Tyr | SEQ ID NO: 28 |
| Analogue 12 | Pro-Arg-Val-Tyr-Ile-His-Pro-Phe | SEQ ID NO: 29 |
| Analogue 13 | Asp-Arg-Pro-Tyr-Ile-His-Pro-Phe | SEQ ID NO: 13 |
| Analogue 14 | Asp-Arg-Val-Tyr($PO_3$)$_2$-Ile-His-Pro-Phe | SEQ ID NO: 30 |
| Analogue 15 | Asp-Arg-norLeu-Tyr-Ile-His-Pro-Phe | SEQ ID NO: 31 |
| Analogue 16 | Asp-Arg-Val-Tyr-norLeu-His-Pro-Phe | SEQ ID NO: 32 |
| Analogue 17 | Asp-Arg-Val-homoSer-Tyr-Ile-His-Pro-Phe | SEQ ID NO: 33 |

Other particularly preferred embodiments include:

| | | | |
|---|---|---|---|
| 1GD | Ala4-AII(1-7) | DRVAIHP | SEQ ID NO: 38 |
| 2GD | Pro3-AII(1-7) | DRPYIHP | SEQ ID NO: 39 |
| 5GD | Lys3-AII(1-7) | DRKYIHP | SEQ ID NO: 40 |
| 9GD | NorLeu-AII(1-7) | DR(nor)YIHP | SEQ ID NO: 41 |
| GSD 28 | Ile$^8$-AII | DRVYIHPI | SEQ ID NO: 42 |
| | Ala3aminoPhe6 AII: | RVAIHPF | SEQ ID NO: 43 |
| | Ala3-AIII | RVAIHPF | SEQ ID NO: 44 |
| | Gly$^1$-AII | GRVYIHPF | SEQ ID NO: 45 |
| | NorLeu$^4$-AIII | --RVYnLHPF | SEQ ID NO: 46 |
| | Acpc$^3$-AII | DR(Acpc)YIHPF | SEQ ID NO: 47 |
| GSD 37B | Orn$^2$-AII | D(Orn)VYIHPF | SEQ ID NO: 48 |
| GSD38B | Citron$^2$-AII | D(Citron)VYIHPF | SEQ ID NO: 49 |
| 3GD | Pro$^3$Ala$^4$-AII(1-7) | DRPAIHP | SEQ ID NO: 50 |
| 8GD | Hydroxy-Pro$^3$-AII(1-7) | DRP(OH)AIHP | SEQ ID NO: 51 |

In another embodiment, the polypeptides may be any of those disclosed in US20100055146, incorporated by reference herein in its entirety. In various embodiments, the polypeptide is:

a 4,7-cyclized analog of Angiotensin II (Ang(1-8), or any of its analogues disclosed herein;

a 4,7-cyclized analog of Angiotensin III (Ang(2-8)), or any of its analogues disclosed herein;

a 4,7-cyclized analog of Angiotensin IV (Ang(3-8)), or any of its analogues disclosed herein; or a 4,7-cyclized analog of Ang(1-7), or any of its analogues disclosed herein.

In another embodiment, the methods comprise administering an agonist of the MAS receptor. Any suitable polypeptide or non-polypeptide agonist of the MAS receptor may be used, including but not limited to A(1-7) and analogues thereof, A779 (D-Ala A(1-7); available from Sigma Chemical Co.) and AVE0991, (see, for example, Pinheiro et al., Hypertension. 2004 October; 44(4):490-6. Epub 2004 Aug. 23).

The polypeptides for use in the present invention may be linear or cyclized in any suitable manner, such as those described in WO2008/018792, including but not limited to polypeptides comprising a thioether bridge between positions 4 and 7, or other positions.

The polypeptides may be recombinantly expressed or chemically synthesized using any suitable techniques, which are well within the level of those of skill in the art.

In another aspect, the present invention provides methods for treating erythemas, blisters, rashes, and/or pruritis, comprising administering to a subject in need thereof an amount effective of a polypeptide comprising or consisting of angiotensinogen, angiotensin I (AI), AI analogues, AI fragments and analogues thereof, angiotensin II (AII), AII analogues, AII fragments or analogues thereof, AII $AT_2$ type 2 receptor agonists, or an agonist (polypeptide or otherwise) of the MAS receptor, to treat the erythema, blister, rash, and/or pruritis.

The usage of erythema, blister, rash, and pruritis is as described above; as used herein, these terms do not include wounds (i.e. lacerations or openings of the skin) The erythema, blister, rash, and pruritis may result from any type of exposure of the subject to an injurious agent, including but not limited to those disclosed above.

As used herein, "treating the erythema, blister, rash, and/or pruritis" means accomplishing one or more of the following: (a) limiting the progression or rate of progression in size, area, severity, and/or depth of the erythema, blister, rash, and/or pruritis; (b) reducing size, area, severity, and/or depth of the erythema, blister, rash, and/or pruritis; (c) increasing rate of healing and/or reducing time to healing of the erythema, blister, rash, and/or pruritis; and (d) healing of the erythema, blister, rash, and/or pruritis.

All embodiments and combinations of embodiments of polypeptides and agonists of the MAS receptor described above can be used in this aspect of the invention. In a most preferred embodiment, the polypeptide comprises or consists of at least 5 contiguous amino acids of Asp-Arg-Nle-Tyr-Ile-His-Pro (SEQ ID NO: 14) (Nle3A(1-7)), including but not limited to Asp-Arg-Nle-Tyr-Ile (SEQ ID NO: 16), Asp-Arg-Nle-Tyr-Ile-His (SEQ ID NO: 17), and most preferably Asp-Arg-Nle-Tyr-Ile-His-Pro (SEQ ID NO: 14).

In another aspect, the present invention provides methods for treating a disorder selected from the group consisting of contact dermatitis, psoriasis, eczema, acne, skin changes such as rashes (for example, from viral infection or autoimmune disease) and athlete's foot, comprising administering to a subject in need thereof an amount effective of a polypeptide comprising or consisting of angiotensinogen, angiotensin I (AI), AI analogues, AI fragments and analogues thereof, angiotensin II (AII), AII analogues, AII fragments or analogues thereof, AII $AT_2$ type 2 receptor agonists, or an agonist (polypeptide or otherwise) of the MAS receptor, to treat the disorder.

All embodiments and combinations of embodiments of polypeptides and agonists of the MAS receptor described above can be used in this aspect of the invention. In a most preferred embodiment, the polypeptide comprises or consists of Asp-Arg-Nle-Tyr-Ile (SEQ ID NO: 16), Asp-Arg-Nle-Tyr-Ile-His (SEQ ID NO: 17), or most preferably Asp-Arg-Nle-Tyr-Ile-His-Pro (SEQ ID NO: 14).

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "contact dermatitis" is a skin reaction (dermatitis) resulting from exposure to allergens (allergic contact dermatitis) or irritants (irritant contact dermatitis). Symptoms of contact dermatitis include, but are not limited to, rashes, blisters, welts, hives, pruritis, and burning skin. The allergen or irritant may be of any sort, including but not limited to food, insect bites or stings, poison ivy, poison oak, poison sumac, soaps, detergents, cleaning products, solvents (including but not limited to alcohol, turpentine, esters, acetones, ketones), metalworking fluids, latex, kerosene, cosmetics, nickel, gold, and chromium.

Symptoms of psoriasis include, but are not limited to, scaly patches on the skin, skin plaques (raised areas of inflamed skin covered with scaly skin), exfoliation of the skin, severe itching, swelling, pain, and pustules.

Symptoms of eczema include, but are not limited to, dryness and recurring skin rashes, redness, skin edema, itching and dryness, crusting, flaking, blistering, cracking, oozing, and bleeding.

Symptoms of athlete's foot include, but are not limited to scaling, flaking, itching, blisters, cracked skin, pain, and swelling.

Symptoms of acne include, but are not limited to, scaly red skin (seborrhea), blackheads and whiteheads (comedones), pinheads (papules), pustules, and nodules.

Viral diseases and autoimmune disorders lead to non-wound skin changes, such as rashes, blisters, welts, hives, pruritis, and burning skin, which can be treated by the methods of the invention.

The polypeptide may be administered in any suitable dose as determined in light of all relevant factors. In one embodiment of all aspects of the invention, the polypeptide, or salt thereof, is administered in a pharmaceutical formulation at a concentration of about 0.001% to about 3% on a weight (mg)/volume (ml) basis, or on a weight/weight (mg) basis. In various further embodiments, the polypeptide, or salt thereof, is administered in a pharmaceutical formulation at a concentration of about 0.005% to about 3%; about 0.01% to about 3%; about 0.05% to about 3%; about 0.01% to about 3%; about 0.5% to about 3%; about 1% to about 3%; about 2% to about 3%; about 0.005% to about 2%; about 0.01% to about 2%; about 0.05% to about 2%; about 0.01% to about 2%; about 0.5% to about 2%; about 1% to about 2%; about 0.005% to about 1%; about 0.01% to about 1%; about 0.05% to about 1%; about 0.01% to about 1%; about 0.5% to about 1%; about 0.005% to about 0.75%; about 0.01% to about 0.75%; about 0.005% to about 0.75%; about 0.01% to about 0.75%; about 0.03% to about 1%; about 0.03% to about 0.75%; about 0.03% to about 0.5%; about 0.03% to about 0.25%; about 0.03% to about 0.1%; about 0.03% to about 0.075%; about 0.03% to about 0.05%; and about 0.03%; all on a weight (mg)/volume (ml) basis, or on a weight/weight (mg) basis.

In all aspects of the invention, the polypeptide or salt thereof may be administered by any suitable route, such as systemic administration (including oral administration); preferably via topical administration. In one embodiment, the methods of the invention can comprise administering a topical formulation as often as deemed appropriate, i.e.: once per day, twice per day, etc. The methods may further comprise administration of the polypeptide, or salt thereof for as longed as deemed desirable by an attending physician. For administration, it is preferred that the topical formulation form a continuous film covering the affected area. In a preferred embodiment, the topical formulation is applied with a thickness of approximately 0.25 to 2 mm; preferably 0.5 to 1.5 mm; preferably about 1 mm in thickness.

In one embodiment of all aspects of the invention, the topical administration comprises administration in a formulation selected from the group consisting of hydrogels, creams, viscoelastics, ointments, pastes, and lotions. The formulations may be applied in any suitable manner, which may include any wound dressings to seal in the formulation deemed appropriate by the human patient or caregiver. Exemplary such dressings, include, but are not limited to, semipermeable films, foams, hydrocolloids, and calcium alginate swabs.

In another embodiment of all aspects of the invention, the topical formulation comprises about 0.5% to about 4% hydroxyethyl cellulose (HEC) on a weight (mg)/volume (ml) basis, or on a weight/weight (mg) basis. In various further embodiments, the topical formulation may comprise about 1% to about 3% HEC, or about 2% HEC, on a weight (mg)/volume (ml) basis, or on a weight/weight (mg) basis.

In all aspects of the invention, the polypeptides, or salt thereof may be administered together with one or more (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The peptides may be administered with a lyoprotectant, e.g. sucrose, sorbitol or trehalose. In certain embodiments, the peptides may be administered with a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the peptides may be administered with a bulking agent, like glycine. In yet other embodiments, the peptides may be administered with a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The peptides may be administered with a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the peptides may be administered with a stabilizer, e.g., a molecule which, when combined with the peptide substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride, paraben, and combinations of methyl paraben and propyl paraben.

In all aspects and embodiments of the invention, suitable acids which are capable of forming salts with the polypeptides include, but are not limited to, inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming salts with the peptides include, but are not limited to, inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

The polypeptides or salts thereof can further be derivatized to provide enhanced half-life, for example, by linking to polyethylene glycol. The peptides or salts thereof may comprise L-amino acids, D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties.

The polypeptides may be the sole active agent in the pharmaceutical composition, or the composition may further comprise one or more other active agents suitable for the desired treatment. The methods may be used in conjunction with other therapies suitable for treating the relevant disorder.

The methods may include any other embodiments as disclosed in the example that follows. Such embodiments may be used in any combination in the methods of the invention, unless the context clearly dictates otherwise.

Example 1. Effects of Nle A(1-7) ("USB001") Administration on Skin Injury Caused by Low-Penetrating Radiation in a Guinea Pig Model

ABBREVIATIONS (a) cGy: centi-Gray, 100 cGy=1 Gy.
(b) Gray: The International System of Units (SI) for radiation measurement is now the official system of measurement and uses the "gray" (Gy).

Epithelial injury following low-penetrating radiation can result in lesions from direct exposure or indirectly by damage to epithelial progenitor cells that would otherwise contribute to healing and inflammation. In this study, we evaluated changes in the response of the skin of guinea pigs (a tight skinned rodent with skin architecture similar to human) to low-penetrating x-ray radiation. Low-penetrating radiation was delivered via the XRAD320ix Biological Irradiator configured with instrument collimator removed and with the use of a lead shield to determine a 4 cm by 4 cm area wound. These changes in skin response were evaluated in guinea pigs receiving no treatment, guinea pigs administered placebo (2% hydroxyethylcellulose with preservatives 0.1% methyl paraben and 0.02% propyl paraben)

and guinea pigs administered USB001 (0.03% NorLeu$^3$-A (1-7) formulated in 2% hydroxyethylcellulose with preservatives 0.1% methyl paraben and 0.02% propyl paraben). Administration of placebo and USB001 took place post-irradiation at predetermined time points corresponding to the onset of erythema. Our results demonstrate that USB001 administration serves to prevent development of wounds in this model.

The guinea pig skin model was developed using 50 kVp x-rays exposure via the XRAD320ix Biological Irradiator. The XRAD320ix was configured without a filter and with the instrument collimator removed. The exposure was on the left side of the guinea pig starting at the forward leg and moving caudally for 4 cm. In this study, the area to be exposed by the attenuated x-ray was defined by lead shielding which allows a 4 cm by 4 cm field of exposure. Endpoints will include skin changes scored on the Kumar Scale and histological changes. Treatment was initiated to coincide with two time points: time at which average Kumar score was ≥1.5 (coinciding with first observation of erythema). Treatment continued until necropsy.

At the end of the study, all tissues were stored at −80° C. in RNALater™ or in formalin at room temperature until processing. Histology slides and fixed remaining tissues were stored appropriately.

Summary of the Test System

Species: Guinea Pig

Strain: Hartley

Source: Charles Rivers

Animal Model of Cutaneous Injury: A 4 cm by 4 cm exposure area (x-ray) defined by a 4 cm by 4 cm opening in a lead shield.

Description of the Animal Test System: Exposure of upper left body starting at the forward leg, approximately 0.3 cm from the spine extending 4 cm in each direction Number of animals per group: 3 in wound dressing only; 4 in placebo and USB001

Sex: Male

Day$_0$ Weight: 450-550 grams

Age at Irradiation: 8-12 weeks

Housing: Number per cage: 1

Feed: Standard laboratory chow

Water: Provided ad libitum

Identification: Per Institution methods

Photoperiod: Diurnal; 12 hours light, 12 hours dark (12L/12D)

Minimum Acclimatization Period: At least seven days in-house prior to start of the study The purpose of the study was to characterize changes in the response of skin to radiation injury (erythema, desquamation, induration, etc) by administration of USB001. Administration began at the first observation of erythema following exposure to low-penetrating radiation. The start of erythema was the time at which the average Kumar score for the group was ≥1.5.

Administration of USB001 or placebo (2% hydroxyethyl cellulose with 0.1% methyl paraben and 0.02% propyl paraben) occurred from the time of erythema to necropsy at day 30. Wound dressings were changed as required. Clinical endpoints of the cutaneous response to radiation (erythema, desquamation, and induration) are used to define the response profile. The scoring system is found on Table 3.

TABLE 3

Assessment Criteria: Kumar Scale
Semi Quantitative Skin Damage Scores (Kumar et al., 2008)

| Score | Skin Changes |
|---|---|
| 1.0 | No Effect |
| 1.5 | Minimal erythema, mild dry skin |
| 2.0 | Moderate erythema, dry skin |
| 2.5 | Marked erythema, dry desquamation |
| 3.0 | Dry desquamation, minimal dry crusting |
| 3.5 | Dry desquamation, dry crusting, superficial minimal scabbing |
| 4.0 | Patchy, moist desquamation, moderate scabbing |
| 4.5 | Confluent moist desquamation, ulcers, large deep scabs |
| 5.0 | Open wound, full thickness skin loss |
| 5.5 | Necrosis |

Induction of Dermal Radiation Exposure

The guinea pig model was used to measure radiation injury after exposure to local low-penetrating radiation at low, medium or high dose (50 kVp at 30 mAmps, 6.5 Gy/minute via XRAD320ix X-Ray) for a total dose of 30 Gy. Hair was removed from the back of the animal by light shaving followed by depilation with Nair™ for three minutes (removal with warm water) to allow hair removal without nicking the skin. The guinea pig was lightly anesthetized (Ketamine/Xylazine) just before the exposure begins to produce immobilization. Animals were administered localized irradiation at various doses to elicit an erythemic response. The low penetrating x-ray was localized in a 4 cm by 4 cm area using a four millimeter (4 mm) thick lead shield. The area exposed was determined by a 4 cm by 4 cm opening in the lead shield. The exposure area was traced on the day of irradiation and the corners were tattooed. The construct is shown below. At study completion (30 days), the tissue was harvested and divided into 4 quadrants.

Radiation Exposure Via XRAD320ix X-Ray

Animals were administered localized irradiation at various doses to elicit an erythemic response. To verify x-ray beam homogeneity, Gafchromic (EBT2) film was exposed at the start and again at the end of each day's irradiation schedule. A Gafchromic (EBT2) film exposure was not performed before or after each individual exposure. The low penetrating x-ray will be localized in a 4 cm by 4 cm area using a 4 mm thick lead shield. In order to ensure close proximity between the lead shield and the guinea pig, the animals were placed on a bed of bubble wrap covered with Kay Dry™.

Treatment with MCM

Treatment with USB001 (300 mcg/ml in 2% hydroxyethyl cellulose with 0.1% methyl paraben or 0.02% propyl paraben) or placebo was initiated at erythema. 1.2 ml of treatment was administered over the 16 cm$^2$ area of radiation exposure using a 3 mL syringe daily until necropsy.

All of the animals were observed for adverse events such as loss of appetite, weight loss, motility/lethargy, and other clinical signs related to the species of choice. All of the animals were weighed.

Clinical Observations

All of the animals were observed for clinical signs of abnormality immediately after exposure to radiation and daily until the end of necropsy. On selected day, the exposed 4 cm by 4 cm of the skin was measured in 4 dimensions (2 measures from corner to corner and 2 measures from edge to edge), as exemplified in FIG. 1 (Withers et al, 1977).

Protocols for in-Life Assessment of Cutaneous Injury
Evaluation of Radiation-Induced Dermal Injury The irradiated area was assessed by observation daily using the Kumar scale for erythema, edema and ulceration (Table 3). The score was assessed daily by blinded observers. On selected days, the exposed 4 cm by 4 cm of the skin was measured in 4 dimensions (2 measures from corner to corner and 2 measures from edge to edge; FIG. 1 (Withers et al, 1977). The abbreviations for the measures in FIG. 1 are: A-D=from the skin score A quadrant to skin score D quadrant; B-C=from the skin score B quadrant to the skin score C quadrant; A-S=abdominal to spine; C-C=cephalic to caudal. The four measurements were multiplied and divided by the value of the same calculation in the non-irradiated controls.

The results from gross evaluation level of the skin after exposure to 32 Gy low penetrating radiation can be found in FIG. 2. When treatment was started at erythema, there was an increase in contracture on days 10-12. This may be due to a rapid replacement of fibroblasts and/or improved vascularization in the dermis resulting from treatment with USB001 that were killed at the time of radiation exposure. There was an improvement in Kumar scores with treatment starting either at erythema (FIG. 2). These data show that treatment with USB001 prevented development of any wound in the test animals during the study, while control animals developed wounds during the study. The development of lesions in the controls included moist desquamation and loss of integrity of the epidermis. This was prevented by early application of the active product. USB001 reduced the post-treatment extent, severity, and duration of wound development compared to control treated animals.

Necropsy

Figure 3:
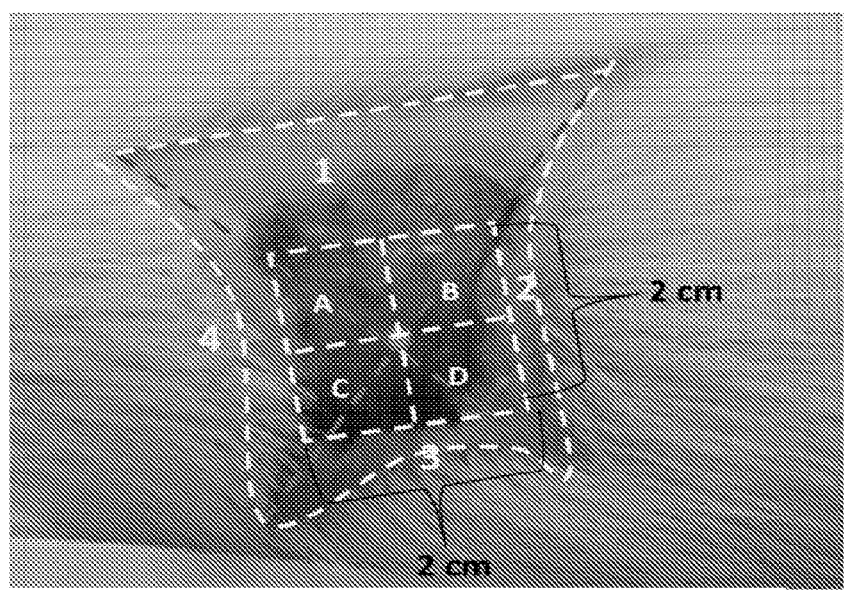
FIG. 3 shows a necropsy diagram of guinea pig skin. The center point of the diagonal cross axes was used to determine the internal 2 cm by 2 cm area.

At necropsy, the inner 2 cm by 2 cm of the irradiated area (4 cm by 4 cm) was cut into 4 (four) quadrants. The inner 2 cm by 2 cm area was measured based upon the center point of the cross axes of the initial corner marks. Two of the quadrants were fixed in formalin (B and D) for histological preparation, and two of the quadrants (A and C) were placed in RNALater™ in thin strips (approximately 2 mm wide) to allow uptake. The remaining area of radiation exposure (outside of the inner 2 cm by 2 cm area) was also cut into 4 pieces, two placed in formalin (3 and 4) and two in RNALater™ (1 and 2). (See FIG. 3). Hematoxylin and eosin stained slides were used to assess inflammation in the dermis. Inflammation appeared and resolved as part of a normal healing process. Prolonged inflammation contributes to continued dermal injury as a result of radiation. Use of USB 001 significantly reduced inflammation compared with placebo (FIG. 2).

REFERENCES FOR EXAMPLE 1

Kumar, S., Kolozsvary, A., Kohl, R., Lu, M., Brown, S., & Kim, J. H. (2008). Radiation-induced skin injury in the animal model of *scleroderma*: implications for post-radiotherapy fibrosis. Radiation Oncology, 3:40-47.

Ouhtit, A., Muller, H. K., Davis, D. W., Ullrich, S. E., McConkey, D., & Ananthaswamy, H. N. (2000). Temporal events in skin injury and the early adaptive responses in ultraviolet-irradiated mouse skin. Am J Pathol, 156(1): 201-207.

Withers H R, Flow B L, Huchton J I, Hussey D H, Jardin J H, Mason K A, Raulston G L, Smathers J B. (1977). Effect of dose fractionation on early and late skin responses to γ-rays and neutrons. Intl. Journal. Radiation Oncology Biol. Phys. 3:227-233.

Example 2

Figure 4:
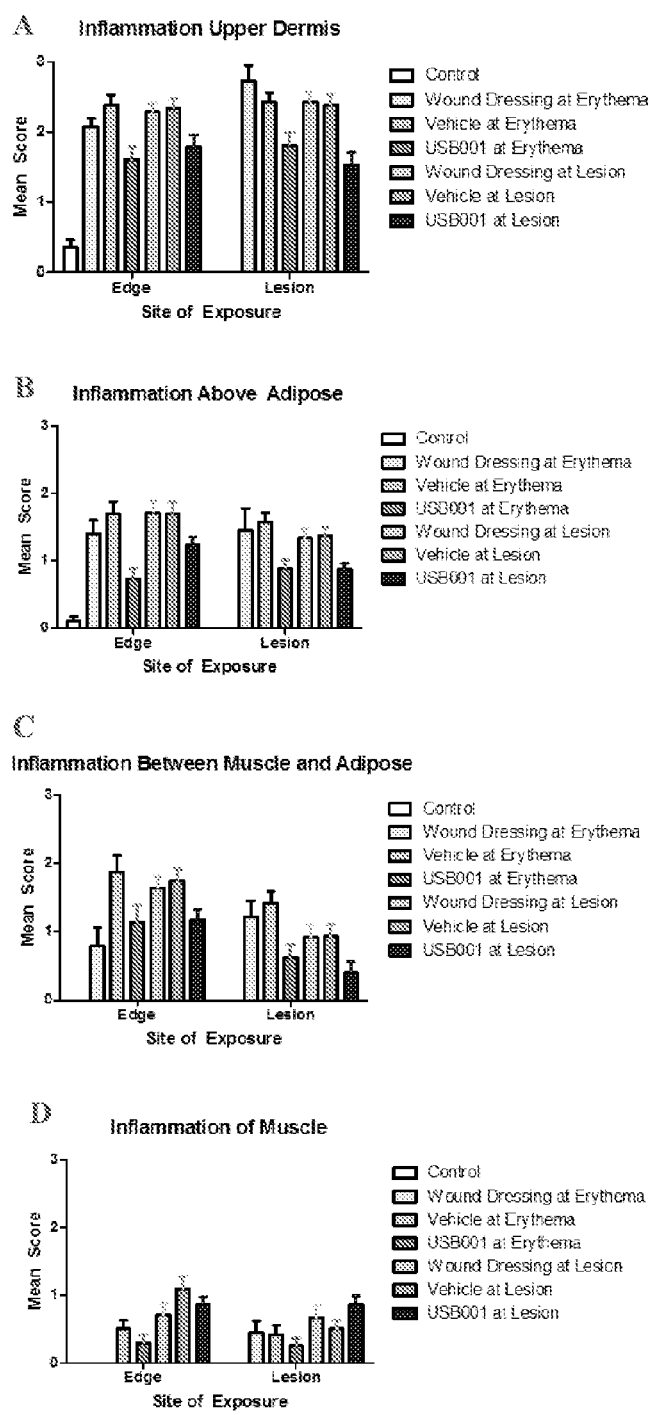
FIGS. 4A-D show a summary of data on histological sections that were prepared at day 30 and evaluated for inflammation in the upper dermis (4A), above the adipose (4B), between the muscle and adipose (4C) and in the muscle (panniculus carnosus) (4D). The control group consists of non-irradiated, non-treated animals necropsied on day 30.
Figure 5:
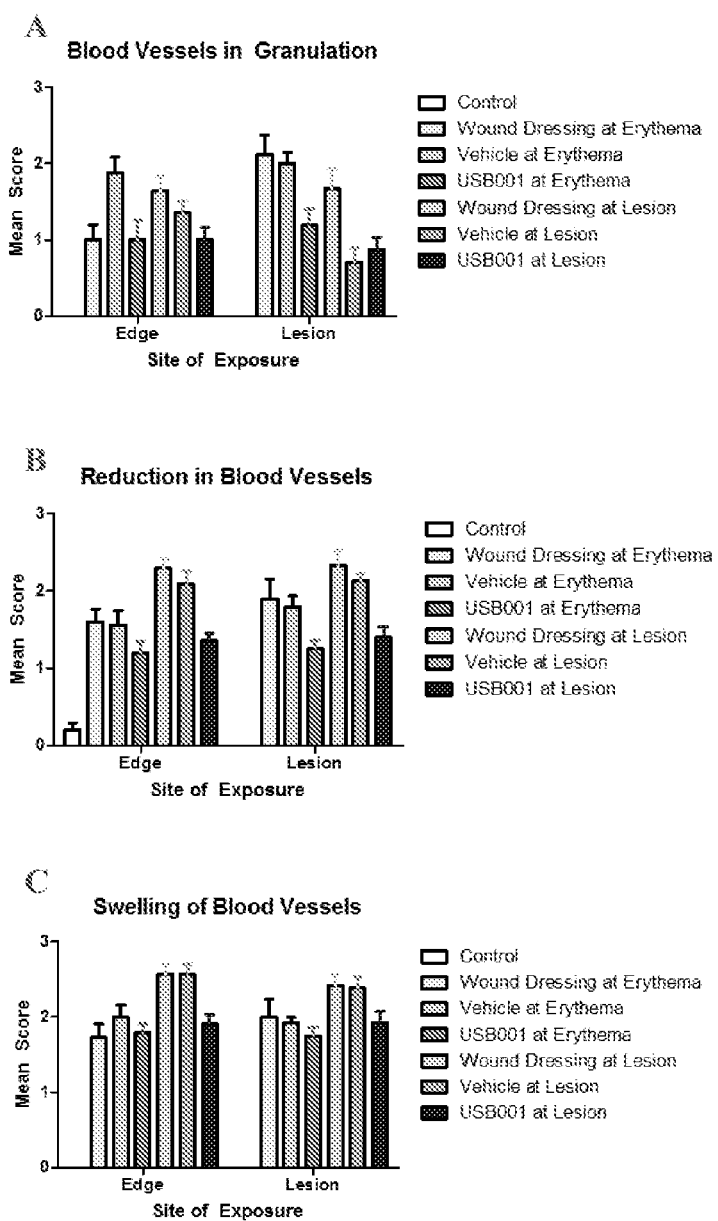
FIGS. 5A-C show a summary of data on histological sections that were prepared at day 30 and evaluated for the amount of granulation tissue as measured by blood vessels (5A), reduction of blood vessels within the dermis (5B) and fibrosis under the muscle (5C). The control group consists of non-irradiated, non-treated animals necropsied on day 30.

Inflammation was assessed at three sites within the dermal tissue: at the upper dermis (FIG. 4A), above the adipose (FIG. 4B), and between the adipose and the panniculus carnosus (FIG. 4C), using methods disclosed for Example 1. Inflammation in the upper dermis, lower dermis (above adipose) and between the adipose and muscle was decreased relative to controls when USB001 treatment (as disclosed above) was initiated at erythema (FIG. 4A). Inflammation at the level of the muscle was unchanged. Further, the formation of granulation tissue as a response to injury as well as changes to blood vessels in the lower dermis (reduction in number and increased swelling) was also assessed histologically (FIG. 5).

As with inflammation, blood vessel formation was affected by USB001. Within the lesion, the amount of granulation tissue as measured by blood vessels in granulation was reduced at the edge and at the center of the wound compared to controls when treatment USB001 was started at erythema (FIG. 5A). When tissues are irradiated, there is a reduction in blood vessels observed within the dermis (FIG. 5B). Treatment with USB001 starting either at erythema increased new blood vessel formation, thereby restoring blood flow. This increase was seen at both the edge of the irradiated area and at the lesion when treatment was started at loss of dermal integrity and at the lesion when treatment was started at erythema with controls. Initiation of treatment with USB001 at erythema did not reduce swelling of the blood vessels compared with controls (FIG. 5C).

Figure 6:
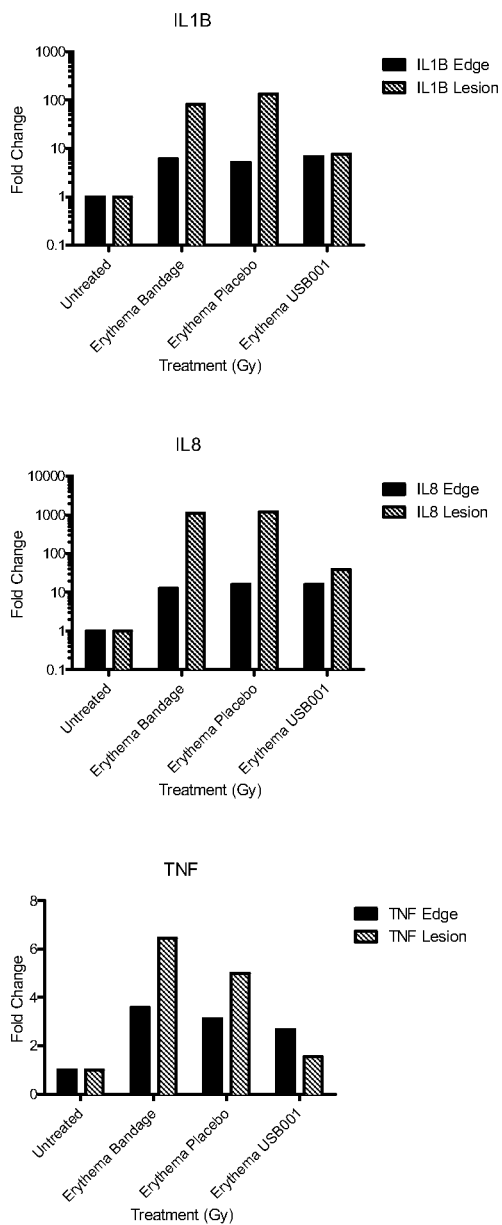
FIGS. 6A-C show a summary of data on expression of genes for inflammatory cytokines measured by RT-PCR at day 30 and evaluated the expression of interleukin 1 (6A), interleukin 8 (6B) and tumor necrosis factor (6C). The control group consists of non-irradiated, non-treated animals necropsied on day 30. The y axis is logarithmic.

In support of the reduced inflammation, expression of inflammatory genes was reduced at the lesion with the site was treated with USB001 starting at erythema (FIG. 6).

We claim:

1. A method for limiting development of a skin wound, comprising administering to a subject that has been exposed to an injurious agent and has developed a pre-wound indication selected from the group consisting of erythemas, blisters, rashes, and pruritis prior to treatment as a result of exposure to the injurious agent, but has not yet developed a skin wound, an amount effective of Asp-Arg-Nle-Tyr-Ile-His-Pro (SEQ ID NO: 14), or a salt thereof, to limit development of a skin wound.

2. The method of claim 1, wherein the subject is a human subject.

3. The method of claim 1, wherein the injurious agent is selected from the group consisting of allergens, skin contact with an irritant, psoriasis, eczema, acne, excessive sun exposure, friction due to chafing of skin, exposure to ionizing radiation, friction on the skin, heat exposure, cold exposure, chemical exposure, contact dermatitis, vesicants, crunching, pinching, or squeezing of the skin; scabies, swimmers' itch, athlete's foot, exposure to poison ivy, exposure to poison oak; body, pubic, or head lice; insect hives, abrasion, contusion, dehydration, excoriation, ultrasound, viruses, autoimmune disease, and xerosis.

4. The method of claim 1, wherein the injurious agent comprises friction on the skin.

5. The method of claim 1, wherein the treating comprises slowing the time to wound development resulting from exposure to the injurious agent.

6. The method of claim 1, wherein limiting development of the skin wound comprises decreasing the severity or decreasing the rate of progression of severity of a subsequently developed wound resulting from exposure to the injurious agent.

7. The method of claim 1, wherein limiting development of the skin wound comprises preventing wound development resulting from exposure to the injurious agent.

8. A method for treating erythemas, blisters, rashes, and/or pruritis, comprising administering to a subject in need thereof an amount effective to treat the erythema, blister, rash, and/or pruritis of Asp-Arg-Nle-Tyr-Ile-His-Pro (SEQ ID NO: 14), or a salt thereof.

9. The method of claim 8, wherein the treating comprises limiting the progression in size, area, and/or depth of the erythema, blister, rash, and/or pruritis.

10. The method of claim 8, wherein the treating comprises reducing size, area, and/or depth of the erythema, blister, rash, and/or pruritis.

11. The method of claim 8, wherein the treating comprises increasing rate of healing and/or reducing time to healing of the erythema, blister, rash, and/or pruritis.

12. The method of claim 8, wherein the treating comprises healing of the erythema, blister, rash, and/or pruritis.

13. A method for treating a disorder selected from the group consisting of contact dermatitis, psoriasis, eczema, acne, and athlete's foot, comprising administering to a subject in need thereof an amount effective to treat the disorder of Asp-Arg-Nle-Tyr-Ile-His-Pro (SEQ ID NO: 14), or a salt thereof.

14. The method of claim 13, wherein the method is used to treat contact dermatitis.

15. The method of claim 13, wherein the method is used to treat psoriasis.

16. The method of claim 13, wherein the method is used to treat eczema.

17. The method of claim 13, wherein the method is used to treat acne.

18. The method of claim 13, wherein the method is used to treat athlete's foot.

19. The method of claim 1, wherein the polypeptide is administered in a pharmaceutical formulation at a concentration of about 0.001% to about 3% on a weight (mg)/volume (ml) basis, or on a weight/weight (mg) basis.

20. The method of claim 1, wherein the polypeptide is administered topically.

21. The method of claim 20, wherein the topical administration comprises administration in a formulation selected from the group consisting of hydrogels, creams, viscoelastics, ointments, pastes, and lotions.

22. The method of claim 20, wherein the topical formulation comprises about 0.5% to about 4% hydroxyethyl cellulose (HEC) on a weight (mg)/volume (ml) basis, or on a weight/weight (mg) basis.

* * * * *